United States Patent
Pang et al.

(10) Patent No.: US 6,303,579 B1
(45) Date of Patent: Oct. 16, 2001

(54) USE OF CALPAIN INHIBITORS TO TREAT OCULAR NEURAL PATHOLOGY

(75) Inventors: Iok-Hou Pang, Grand Prairie; Michael A. Kapin, Arlington; Louis DeSantis, Jr., Fort Worth, all of TX (US)

(73) Assignee: Alcon Laboratories, Inc., Fort Worth, TX (US)

( * ) Notice: Subject to any disclaimer, the term of this patent is extended or adjusted under 35 U.S.C. 154(b) by 0 days.

(21) Appl. No.: 09/284,074

(22) PCT Filed: Sep. 19, 1997

(86) PCT No.: PCT/US97/16742

§ 371 Date: Apr. 5, 1999

§ 102(e) Date: Apr. 5, 1999

(87) PCT Pub. No.: WO98/18485

PCT Pub. Date: May 7, 1998

Related U.S. Application Data

(60) Provisional application No. 60/029,353, filed on Oct. 31, 1996.

(51) Int. Cl.[7] .......................... A61K 38/00; A61K 39/00; A61K 39/38
(52) U.S. Cl. ........................ 514/19; 424/184.1; 424/185.1
(58) Field of Search ............................ 424/184.1, 185.1; 514/19

(56) References Cited

U.S. PATENT DOCUMENTS

| | | |
|---|---|---|
| 5,081,284 | 1/1992 | Higuchi et al. . |
| 5,189,144 | 2/1993 | Asada et al. . |
| 5,328,909 | 7/1994 | Ando et al. . |
| 5,336,783 | 8/1994 | Omura et al. . |
| 5,340,922 | 8/1994 | Nixon et al. . |
| 5,422,359 | 6/1995 | Ando et al. . |
| 5,444,042 | 8/1995 | Bartus et al. . |
| 5,486,623 | 1/1996 | Zimmerman et al. . |
| 5,498,616 | 3/1996 | Mallamo et al. . |
| 5,506,243 | 4/1996 | Ando et al. . |
| 5,514,694 | 5/1996 | Powers et al. . |
| 5,541,290 | 7/1996 | Harbeson et al. . |

FOREIGN PATENT DOCUMENTS

| | | |
|---|---|---|
| 0 520 336 A2 | 12/1992 | (EP) . |
| 0 580 161 A1 | 1/1994 | (EP) . |
| WO 92/11850 | 7/1992 | (WO) . |
| WO 94/00095 | 1/1994 | (WO) . |
| WO 95/26506 | 10/1995 | (WO) . |

OTHER PUBLICATIONS

Azarian et al, *Current Eye Research*, vol. 14, pp. 731–735 (1995).*

Azarian et al, *J of Cell Sci.*, vol. 105, pp. 787–798 (1993).*

Karlsson et al, *Neuroscience Letters*, vol. 141, pp. 127–129, (1992).*

Blomgren et al., *Neuroscience Letters*, vol. 112, pp. 179–183, (1990).*

Azarian et al., "Calpain activity in the retinas of normal and RCS rats", *Current Eye Research*, vol. 14, pp. 731–735 (1995).

Azarian et al., "Characterization of calpain II in the retina and photoreceptor outer segments", *Journal of Cell Sciences*, vol. 105, pp. 787–798 (1993).

Bartus et al., "Calpain Inhibitor AK295 Protects Neurons From Focal Brain Ischemia", *Stroke*, vol. 25, No. 11, pp. 2265–2270 (1994).

Bartus et al., "Postischemic Administration of AK275, a Calpain Inhibitor, Provides Substanial Protection Against Focal Ischemic Brian Damage", *Journal of Cerebral Blood Flow and Metabolism*, vol. No. 14, pp. 537–544 (1994).

Blomgren et al., "Calpain and calpastatin activity in the optic pathway", *Neuroscience Letters*, 112, pp.179–183 (1990).

Brorson et al., "Delayed Antagonism of Calpain Reduces Excitotoxicityin Cultured Neurons", *Stoke*, vol. 26, No. 7, pp. 1259–1266 (1995).

Caner, et al. "Attenuation of AMPA–induced neuroxtoxicity by a calpain inhibitor", *Brain Research*, vol. 607, pp. 354–356 (1993).

Hiramatsu et al., "Improved Posthypoxic Recovery of Synaptic Transmission in Gerbil Neocortical Slices Treated With a Calpain Inhibitor", *Stroke*, vol. 24, No. 11, pp. 1725–1728 (1993).

Hong et al., "Neuroprotection With a Calpain Inhibitor in a Model of Focal Cerebral Ischemia", *Stroke*, vol. 25, No. 3, pp. 663–669 (1994).

Karlsson et al., "Slow axonal transport of soluble proteins and calpain in retinal ganglion cells of aged rabbits", *Neuroscience Letters*, vol. 141, pp. 127–129 (1992).

Lee et al., "Inhibition of proteolysis protects hippocampal neurons from ischemia", Proceedings of the National Academy of Sciences USA, vol. 88, pp. 7233–7237 (1991).

Minami et al., "Effects of inhibitors of protein kinase C and calpain in experimental delayed cerebral vasospasm", *Journal of Neurosurgery*, vol. 76, pp. 111–118 (1992).

Murachi, Takashi, "Intracellular Regulatory System Involving Calpain And Calpastatin", *Biochemistry International*, vol. 18, No. 2, pp. 263–294 (1989).

(List continued on next page.)

Primary Examiner—Avis M. Davenport
(74) Attorney, Agent, or Firm—Sally S. Yeager

(57) ABSTRACT

The invention provides pharmaceutical compositions containing calpain inhibitors and methods of using these calpain inhibitors to prevent or ameliorate ocular neural tissue disease or damage.

7 Claims, No Drawings

OTHER PUBLICATIONS

Nixon, Ralph A., "Calcium–Activated Neutral Proteinases as Regulators of Cellular Function", *Annals of the New York Academy of Sciences*, vol. 568, pp. 198–208 (1989).

Persson et al., "Immunohistochemical localization of calpains and calpastatin in the rabbit eye", *Brain Research*, vol. 611, pp.272–278 (1993).

Rami et al., "Protective effects of calpain inhibitors against neuronal damage caused by cytotoxic hypoxia in vitro and ischemia in vivio", *Brain Research*, vol. 609, pp. 67–70 (1993).

Saido et al., "Calpain: new perspectives in molecular diversity and physiological–pathological involvement", *FASEB Journal*, vol. 8, pp. 814–822 (1994).

Shields et al, "Calpain activation optic nerve", 27th Annual Meeting of the American Society For Neurochemistry,Philadelphia, PA, Mar.2–6, 1996, *Journal of Neurochemistry*, 66 (suppl 1) (1996). and Abstrac.

Shields et al., "Calpain's role in optic neuritis", 26th Annual Meeting of the Society for Neuroscience, Washington DC, No. 16–21, 1996, *Society for Neuroscience Abstracts*, 22 (1–3).

Siman et al., "Calpain I Activation Is Specifically Related to Excitatory Amino Acid Induction of Hippocampal Damage", *Journal of Neuroscience*, vol. 9, No. 5, pp. 1579–1590 (1989).

Suzuki et al., "Calcium–activated neutral protease and its endogenous inhibitor", *FEBS Letters*, vol. 220, No. 2, pp. 271–277(1987).

Wang et al., "Calpain inhibition: an overview of its therapeutic potential", *Trends in Pharmacological Sciences*, vol. 15, pp. 412–419 (1994).

Wang, "An alpha–mercaptoacrylic acid derivative is a selective nonpeptide cell–permeable calpain inhibitor and is neuroprotective", *Proc. Natl. Acad. Sci. USA*, vol. 93, pp. 6687–6692 (1996).

Zimmerman et al., "Two–stage autolysis of the catalytic subunit initiates activation of calpain I", *Biochimica et Biophysica Acta*, vol. 1078, pp. 192–198 (1991).

* cited by examiner

USE OF CALPAIN INHIBITORS TO TREAT OCULAR NEURAL PATHOLOGY

This application is a 371 of PCT/US97/16742 filed Sep. 19, 1997 and also claims priority from the provisional application Ser. No. 60/029,353 filed Oct. 31, 1996.

BACKGROUND OF THE INVENTION

The present invention relates generally to the field of ocular neuroprotectants and more specifically to the use of inhibitors of calcium-stimulated proteases to treat ocular neurodegeneration.

Evidence from various studies suggests that one of the earliest events in the chain of reactions leading to neuronal death caused by ischemia or excitatory amino acid (e.g., glutamate) toxicity is an increase in intracellular free calcium. This intracellular free calcium increase is the consequence of extracellular $Ca^{2+}$ channel opening, release of calcium from intracellular stores and/or energy depletion. Increases in intracellular calcium activate a number of cellular responses and processes that are thought to mediate cytotoxicity, including the activation of phospholipases, kinases, nitric oxide synthases, endonucleases and proteases, such as neutral proteases collectively referred to as the calpains. Additionally, an increase in intracellular calcium is also thought to induce changes in gene expression, such as the up-regulation of calpains.

Calpains are a family of calcium activated cysteine (thiol) proteases which are present in the cytoplasm of many tissues. It is known that there are two distinct classes of isozymes, calpain I and calpain II. These enzymes require $\mu$M and mM levels of calcium, respectively, for their optimal enzymatic activation. Hence, calpain I is also known as $\mu$-calpain and calpain II is also known as m-calpain. Both calpains predominantly exist within cells in the form of an inactive precursor (Suzuki, Calcium-activated neutral protease and its endogenous inhibitor, *FEBS Letters*, volume 220, number 2, pages 271–277 (1987)). The precursor is converted into its active form in the presence of calcium through a self-digestion process which occurs at the N-terminal of the protein (Zimmerman, Two-stage autolysis of the catalytic subunit initiates activation of calpain I, *Biochimica et Biophysica Acta*, volume 1078, pages 192–198 (1991)). Calpain II is the predominant form, but calpain I is found at synapses and is thought to be the form involved in long term potentiation and synaptic plasticity.

Activated calpain hydrolyzes cellular proteins such as cytoskeletal proteins (e.g. spectrin, fodrin, talin, filamin, α-actinin, microtubule-associated proteins), membrane receptors (e.g. epidermal growth factor receptor, estrogen receptor, progesterone receptor, glucocorticoid receptor, platelet-derived growth factor receptor), cell adhesion molecules (e.g. integrin, cadherin, N-CAM), ion transporters (e.g. calcium-ATPase), calmodulin-binding proteins, guanyl nucleotide-binding regulatory proteins (G proteins), kinases (e.g. protein kinase C, myosin light chain kinase, calmodulin-dependent kinase, pp60 src), phosphatases (e.g. calcineurin), phospholipases (e.g., phospholipase C), xanthine oxidase and transcription factors (e.g. Fos, Jun). (See, Saido, Calpain: new perspectives in molecular diversity and physiological-pathological involvement, *FASEB Journal*, volume 8, pages 814–822 (1994).)

It is clear that calpain participates in the control of many inter- and intracellular signal transduction systems. Thus, abnormal activation of calpain can have serious effects on cellular functions and viability (Murachi, Intracellular Regulatory System Involving Calpain And Calpastatin, *Biochemistry International*, volume 18, number 2, pages 263–294 (1989); Nixon, Calcium-Actrvated Neutral Proteinases as Regulators of Cellular Function, *Annals of the New York Academy of Sciences*, volume 568, pages 198–208 (1989)). Indeed, rapid activation of calpain, which occurs during ischemia and during treatment with excitatory amino acids, causes an acute neurotoxicity, apoptosis and neuronal cell death in brain tissues (Siman, Calpain I Activation Is Specifically Related to Excitatory Amino Acid Induction of Hippocampal Damage, *Journal of Neuroscience*, volume 9(5), pages 1579–1590 (1989); Lee, Inhibition of proteolysis protects hippocampal neurons from ischemia, *Proceedings of the National Academy of Sciences USA*, volume 88, pages 7233–7237 (1991)).

Calpain activation has been associated with several neurodegenerative conditions, including those caused by Alllheimer's Disease, Parkinson's Disease, Pick's Disease, traumatic brain injury, subarachnoid hemorrhage, HIV-induced neuropathy, stroke, hypoxia, ischemia, lesions, and exposure to toxins (Wang, Calpain inhibition. an overview of its therapeutic potential, *Trends in Pharmacological Sciences*, volume 15, pages 412–419 (1994); Saido, *FASEB Journal*, volume 8, pages 814–822 (1994)).

Calpain inhibitors have been shown to reduce neuronal damages induced by hypoxia or by amino acid excitotoxicity in brain tissue (Minami, Effects of inhibitors of protein kinase C and calpain in experimental delayed cerebral vasospasm, *Journal of Neurosurgy*, volume 76, pages 111–118 (1992); Caner, Attenuation of AMPA-induced neurotoxicity by a calpain inhibitor, *Brain Research*, volume 607, pages 354–356 (1993); Rami, Protective effects of calpain inhibitors against neuronal damage caused by cytotoxic hypoxia in vitro and ischemia in vivo, *Brain Research*, volume 609, pages 67–70 (1993); Hiramatsu, improved Posthypoxic Recovery of Synaptic Transmission in Gerbil Neocortical Slices Treated With a Calpain Inhibitor, *Stroke*, volume 24, pages 1725–1728 (1993); Hong, Neuroprotection With a Calpain Inhibitor in a Model of Focal Cerebral Ischemia, *Stroke*, volume 25, pages 663–669 (1994); and Bartus, Calpain Inhibitor AK295 Protects Neurons From Focal Brain Ischemia, *Stroke*, volume 25, pages 2265–2270 (1994). Bartus et al. (WO 92/11850) describe several classes of calpain inhibitors and methods for identifying calpain inhibitors in which the enzymatic activity of calpain was assayed by the detection of spectrin breakdown products through Western blot analysis using a spectrin-specific antibody. Various publications in the scientific and patent literature have described numerous chemical classes of calpain inhibitors.

There is increasing evidence which suggests that calpain is present in the retina (Karisson, Slow axonal transport of soluble proteins and calpain in retinal ganglion cells of aged rabbits, *Neuroscience Letters*, volume 141, pages 127–129 (1992); Persson, Immunohistochemical localization of calpains and calpastatin in the rabbit eye, *Brain Research*, volume 611, pages 272–278 (1993); Azarian, Characterization of calpain II in the retina and photoreceptor outer segments, *Journal of Cell Sciences*, volume 105, pages 787–798 (1993); Azarian, Calpain activity in the retinas of normal and RCS rats, *Current Eye Research*, volume 14, pages 731–735 (1995)).

SUMMARY OF THE INVENTION

The present invention is directed to the use of calpain inhibitors to protect ocular neural tissue. In particular the present invention is directed to compositions containing calpain inhibitors and methods of using these compositions to prevent ocular cell damage or diseases due to neurodegenerative disorders of the retina. Such neurodegerative disorders may be caused by ischemia, hypoxia, edema, oxidative injury, metabolic insufficiency, excitotoxicity, trauma and apoptotic cell death. Examples of neurodengenerative disorders of the retina include ischemic retinopathies or optic neuropathies (e.g. AION), commotio retinae, glaucoma, macular degeneration, retinitis pigmentosa, retinal detachment, retinal tears or holes, diabetic retinopathy and iatrogenic retinopathy.

The calpain inhibitors are believed to protect the retinal neurons by inhibiting the destructive action of activated calpain, as described above. The calpain inhibitors may be administered by various means such as orally, parenterally, intraocularly or topically. Various compositions necessary for these various pharmaceutical applications are set forth below. Since there is no currently accepted treatment of the above-mentioned retinopathies, the calpain inhibitors provide a novel means to prevent or reduce retina and optic nerve head damage related to various ocular pathologies.

DETAILED DESCRIPTION OF THE INVENTION

The present invention is directed to compositions and methods of using calpain inhibitors to prevent or ameliorate ocular neuronal tissue damage or pathologies resulting from various cellular insults. As stated above, calpain is believed to be a critical factor involved in the cell's cytotoxic response to ischemia, hypoxia, amino acid excitotoxicity or other attacks on the ocular neuronal tissue.

Calpain is activated by increases in intracellular calcium, which can be effected by all of the above pathological conditions. For example, excessive synaptic levels of glutamate (the major excitatory neurotransmitter in the retina) activate ionotropic excitatory amino acid receptors (which are themselves sodium and calcium ion channels) in the postsynaptic membrane, producing a sustained and elevated influx of sodium and calcium ions into the cell. Sodium influx induces membrane depolarization which opens voltage-gated calcium channels and causes further calcium influx, thus; further increasing the intracellular calcium concentration.

In addition, trauma and ischemia in neuronal tissues can also increase intracellular calcium. At least two different mechanisms are involved. One involves excitotoxicity (resulting from excessive presynaptic release and impaired reuptake of glutamate), thus leading to calcium mobilization. Another mechanism involves the depletion of cellular ATP and the subsequent loss of ion transport regulation across intracellular organelles, as well as across the plasma membrane. These events directly and indirectly increase intracellular calcium and stimulate protease activity of calpain.

Based on calpain's role in neuronal cell death following cellular stress, it is believed that calpain is also involved in various forms of retinopathy or optic nerve pathology related to glaucoma, ischemia, edema or other traumas. It is also believed that an inhibitor of the enzymatic activity of calpain will have therapeutic value in the prevention or treatment of the above-mentioned ocular diseases. As indicated above, the protease activity of calpain is responsible for the hydrolysis of many intracellular proteins which in turn interferes with cellular functions. This interference of normal cellular functions eventually leads to cell death. The present invention provides the use of calpain inhibitors for the protection of ocular neuronal tissue, i.e., the retina and optic nerve.

Molecules from various chemical classes can be used as calpain inhibitors. As used herein, the term "calpain inhibitor" refers to those molecules which retard or inhibit the catalytic action of calpain.

Calpain inhibitors of the present invention are known and have been described in numerous scientific and patent literature. For example, U.S. Pat. No. 5,081,204 (Higuchi), U.S. Pat. No. 5,486,623 (Zimmerman), U.S. Pat. No. 5,498,616 (Mallamo), U.S. Pat. No. 5,506,243 (Ando), and U.S. Pat. No. 5,514,694 (Powers) describe a variety of different chemical entities for the inhibition of calpain including: N-substituted peptidyl compounds, peptidyl ketone heterocyclic ethers, heterocyclic-N-heteroatom methyl ketones, sulfonamide pyrolidines, and peptidyl ketoamides, respectively. Additional examples of calpain inhibitors in the patent literature include WIPO Publication Nos. WO 92/11850 (Cortex Pharmaceutical), WO 94/00095 (Cortex) and WO 95/00535 (Akermes Inc.) which disclose peptide keto compounds, peptide aldehyles and α-ketoamides, respectively. Other examples of calpain inhibitors have been published in European Patent Application Publications. Still other calpain inhibitors in the scientific literature include α-mercaptoacrylic acids, disclosed in *Proc. Natl. Acad. Sci. USA*, volume 93, pages 6687–6692 (1996).

Preferred calpain inhibitors include the following peptide keto-compounds, all of which are disclosed in WIPO Patent Application No. WO 94/00095:

Compound 1 (Example PKC 131)
  $PhCH_2OCO$-leucine-norvaline-$CONH$—$CH_2$-2-pyridyl;
Compound 2 (Example PKC 145)
  $Ph_2CHCO$-leucine-α-aminobutyric acid-$CONH$—$CH_2$-2-pyridyl;
Compound 3 (Example PKC146)
  $Ph_2CHCO$-leucine-α-aminobutyric acid-$CONH$—$(CH_2)_3$-4-morpholinyl;
Compound 4 (Example PKC104)
  $PhCH_2OCO$-leucine-α-aminobutyric acid-$CONH$—$CH_2$-2-pyridyl; and
Compound 5 (Example PKC78)
  $PhCH_2OCO$-leucine-α-aminobutyric acid-$CONH$—$CH_2$—$CH(OH)Ph$.

The most preferred calpain inhibitor is PD 150606, which is disclosed in Wang, *Proc. Natl. Acad. Sci. USA*, volume 93, pages 6687–6692 (1996), described above.

The calpain inhibitors of the present invention may also be determined by various assays described in the literature. The following publications teach various methods for calpain inhibitor elucidation, the entire contents of which are incorporated herein by reference:

1) Wang, An alpha-mercaptoacrylic acid derivative is a selective nonpeptide cell-permeable calpain inhibitor and is neuroprotective, *Proc. Natl. Acad. Sci. USA*, volume 93, pages 6687–6692 (1996);

2) WIPO Publication No. WO 95/00535 (Alkermes, Inc.), Page 47; and

3) WIPO Publication No. WO 92/11850 (Cortex Pharmaceuticals, Inc), Substitute Sheet, Page 49.

The compositions and methods of the present invention use agents which inhibit calpain, for preventing or protecting the retina and optic nerve head from diseases or damages caused by glaucoma, ischemia, trauma or edema.

Calpain inhibitors may be administered systemically, topically, by intraocular injection, intraocular perfusion, periocular injection or retrobulbar injection. When calpain inhibitors are delivered by systemic administration, including oral administration, intramuscular injection, subcutaneous injection, intravenous injection, transdermal administration and transmucosal administration, the daily dosage of calpain inhibitors will range between about 0.01 and 100 milligrams per kilogram body weight per day (mg/kg/day), preferably between about 0.1 and 10 mg/kg/day.

The exact dosage of one or more calpain inhibitor(s) to be administered to the patient will vary, but will be determined by skilled clinicians in the art. Various factors affecting the dosage amount include the actual disease to be treated, the severity of condition, the health of the patient, the potency and specific efficacy of the calpain inhibitor, and so on. The amount dosed, however, will be an "effective amount." As used herein, the term "effective amount" is an amount which inhibits calpain at a level effective for therapy.

The calpain inhibitors of the present invention may be contained in various types of ophthalmic compositions, in accordance with formulation techniques known to those skilled in the art For example, the compounds may be included in solutions, suspensions and other dosage forms adapted for topical, intravitreal or intracameral use.

The ophthalmic compositions of the present invention will include one or more calpain inhibitor(s) of the present invention and a pharmaceutically acceptable vehicle. Aqueous solutions are generally preferred, based on ease of formulation and physiological compatibility. However, the calpain inhibitors of the present invention may also be readily incorporated into other types of compositions, such as suspensions, viscous or semi-viscous gels or other types of solid or semi-solid compositions. The ophthalmic compositions of the present invention may also include various other ingredients, such as buffers, preservatives, co-solvents and viscosity building agents.

An appropriate buffer system (e.g., sodium phosphate, sodium acetate or sodium borate) may be added to prevent pH drift under storage conditions.

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, polyquatemium-1, or other agents known to those skilled in the art. Some of these preservatives, however, may be unsuitable for particular applications, (e.g., benzalkonium chloride may be unsuitable for intraocular injection). Such preservatives are typically employed at a level of from is 0.001 to 1.0% weight/volume ("% w/v").

While at the present time there are no effective methods to effect back of the eye treatment of chronic conditions via topical administration, it is contemplated that such methods will be developed. If topical administration of calpain inhibitors becomes feasible, the dosage generally will range between about 0.001 and 5% weight/volume ("w/v"), preferably between 0.1 and 1% (w/v). Solutions, suspensions, ointments, gels, jellies and other dosage forms adapted for topical administration are preferred. Additionally, calpain inhibitors may be delivered slowly, over time, to the afflicted tissue of the eye through the use of contact lenses. This regimen is generally performed by first soaking the lenses in a calpain inhibitor solution, and then applying the contact lenses to the eye for normal wear.

As used herein, the term "pharmaceutically acceptable carrier" refers to any formulation which is acceptable, i.e., safe and provides the appropriate delivery for the desired route of administration, of an effective amount of at least one calpain inhibitors of the present invention.

The compositions of the present invention are further illustrated in the following formulation examples, calpain inhibitors of the present invention are represented generically in the examples as "Calpain Inhibitor."

EXAMPLE 1

A topical ophthalmic composition useful for treating ocular neural tissue:

| Component | % w/v |
|---|---|
| Calpain Inhibitor | 0.1 |
| Dibasic Sodium Phosphate | 0.2 |
| HPMC | 0.5 |
| Polysorbate 80 | 0.05 |
| Benzalkonium Chloride | 0.01 |
| Sodium Chloride | 0.75 |
| Edetate Disodium | 0.01 |
| NaOH/HCl | q.s., pH 7.4 |
| Purified Water | q.s. 100% |

EXAMPLE 2

A sterile intraocular injection solution useful for treating ocular neural tissue:

| Component | % w/v |
|---|---|
| Calpain Inhibitor | 0.05–5.0 |
| Cremophor EL ® | 10 |
| Tromethamine | 0.12 |
| Mannitol | 4.6 |
| Disodium EDTA. | 0.1 |
| Hydrochloric acid or sodium hydroxide | q.s., pH to 7.4 |
| Water for injection | q.s. 100% |

EXAMPLE 3

A tablet formulation suitable for oral administration, and useful for treating ocular neural tissue:

| Ingredient | Amount per Tablet (mg) |
|---|---|
| Calpain Inhibitor | 200 |
| Cornstarch | 50 |
| Lactose | 145 |
| Magnesium stearate | 5 |

EXAMPLE 4

An systemic injectable solution useful for treating ocular neural tissue:

| Ingredient | Amount |
|---|---|
| Calpain Inhibitor | 200 mg |
| 0.4 M KH$_2$PO$_4$ solution | 2 ml |

-continued

| Ingredient | Amount |
| --- | --- |
| 1 N KOH solution | q.s. to pH 7.0 |
| Water for injection | q.s. to 20 ml |

What is claimed is:

1. A method for treating retinal or optic nerve disease or damage in humans wherein the disease or damage is selected from the group consisting of ischemic retinopathies or optic neuropathies, commotio retinae, glaucoma, macular degeneration, retinitis pigmentosa, retinal detachment, retinal tears or holes, diabetic retinopathy, and iatrogenic retinopathy which comprises administering to a human patient a composition containing an effective amount of one or more calpain inhibitor(s) in a pharmaceutically acceptable vehicle.

2. A method according to claim 1 wherein the disease or damage is glaucoma.

3. A method according to claim 1 wherein the calpain inhibitor is selected from the group consisting of:

PD 150606;

$PhCH_2OCO$-leucine-norvaline-$CONH—CH_2$-2-pyridyl;

$Ph_2CHCO$-leucine-αaminobutyric acid-$CONH—CH_2$-2-pyridyl;

$Ph_2CHCO$-leucine-αaminobutyric acid-$CONH—(CH_2)_3$-4-morpholinyl;

$PhCH_2OCO$-leucine-αaminobutyric acid-$CONH—CH_2$-2-pyridyl; and $PhCH_2OCO$-leucine-αaminobutyric acid-$CONH—CH_2—CH(OH)Ph$.

4. A method according to claim 1, which further comprises administering the composition by intraocular injection, ocular topical application, intravenous injection, oral administration, intramuscular injection, intraperitoneal injection, transdermal, application or transmucosal application.

5. An ocular composition for treating retinal or optic nerve disease or damage in humans wherein the disease or damage is selected from the group consisting of ischemic retinopathies or optic neuropathies, commotio retinae, glaucoma, macular degeneration, retinitis pigmentosa, retinal detachment, retinal tears or holes, diabetic retinopathy, and iatrogenic retinopathy comprising one or more calpain inhibitor(s) in a pharmaceutically acceptable vehicle.

6. A composition of claim 5 wherein the composition is selected from the group consisting of: ocular topical, intraocular injection, intraocular perfusion, periocular injection and retrobulbar injection formulations.

7. composition of claim 5 wherein the composition is a topical ocular formation, and the vehicle selected from the group consisting of: aqueous solutions, suspensions, ointments, gels, and jellies.

* * * * *